United States Patent [19]
Lennon et al.

[11] Patent Number: 5,858,317
[45] Date of Patent: Jan. 12, 1999

[54] METHOD FOR PREPARING CYANOPHOSPHONATE DERIVATIVES FROM PHOSPHORIC ANHYDRIDE AND CYANIDE

[75] Inventors: Patrick J. Lennon, Webster Grove; Sergey G. Vulfson, Chesterfield, both of Mo.

[73] Assignee: Monsanto Company, St. Louis, Mo.

[21] Appl. No.: 996,949

[22] Filed: Dec. 23, 1997

Related U.S. Application Data

[60] Provisional application No. 60/034,512, Dec. 30, 1996.
[51] Int. Cl.$^6$ .............................. C07F 9/40; C07F 9/38; C01B 25/16
[52] U.S. Cl. ..................... 423/302; 558/87; 558/145; 558/166; 558/167; 562/16; 564/281; 564/291; 564/292; 568/9; 568/18; 568/27
[58] Field of Search ............................ 423/302; 558/87, 558/145, 166, 167; 562/16; 564/281, 291, 292; 568/9, 18, 27

[56] References Cited

U.S. PATENT DOCUMENTS

| | | |
|---|---|---|
| 2,402,703 | 6/1946 | Woodstock . |
| 2,702,299 | 2/1955 | Harris . |
| 3,432,277 | 3/1969 | Roesky ....................................... 23/357 |
| 3,812,221 | 5/1974 | Braden et al. ........................... 260/968 |
| 4,221,583 | 9/1980 | Gaertner et al. . |
| 4,568,432 | 2/1986 | Rogers . |

FOREIGN PATENT DOCUMENTS

| | | | |
|---|---|---|---|
| 300 936 | 9/1992 | Germany ......................... C07F 9/40 |
| 96/15135 | 5/1996 | WIPO . |

OTHER PUBLICATIONS

Abstract—Database WPI, Section Ch, Week 7615, Derwent Publications Ltd., London, GB; Class B04, AN 76–27192X, XP002061354 & JP 51 023 225 A (Nippon Chem. Ind. Co. Ltd.), 24 Feb. 1976.

Blanchard, J. "Préparation d–acides beta–amino–ethyl–phosphoniques" *Tetrahedron*, vol. 32, No. 4, 1976, Oxford GB, pp. 455–459, XP002061374.

Chemical Abstracts, vol. 093, No. 12, 22 Sep. 1980, Columbus, Ohio, US; abstract No. 123612, Zhurba, Y.I. et al. "Increase in the stability of silver complexes in the process of simultaneous developing and fixing" and ZH Nauchn, Pirkl. Fotogr.Kinematogr. (ZNPFAG, 00444561); 80; vol. 25(3); pp. 182–5, VSES. Gos.Nauchno–Issled. Proektn. Inst. Khim.–Fotogr. Prom., Moscow; USSR; XP002061352.

Dyatkina, N. et al., Synthesis and antiviral activity of some fluorinated nucleotide derivativers; Nucleoside Nucleotides (Nunud5, 07328311); 94; col. 13 (1–3); pp. 325–337, Engelhardt Inst. Mol. Biol.; Mowcow; 117984, Russia XP002061348.

Kashemirov, B.A. "(E)–(Hydroxyimino)(hydroxymethoxyphosphinyl)acetic acid: Synthesis and pH dependent fragmentation," *Tetrahedron Letters*, vol. 36, No. 52, 1995, Oxford GB, pp. 9437–9440; XP002061351.

Albrecht et al., "Reaction of the Two–Component System Trialkyl Phosphite/Carbon Tetrachloride with Nucleophiles 3. Reaction in Presence of Trialkylammonium Salts," *Z. anorg. allg. Chem.* 552:132–146 (1987) and English language translation.

Kashemirov et al., "Troika Acids: Synthesis, Structure, and Fragmentation Pathways of Novel α–(Hydroxyimino)phosphonacetic Acids," *J. Am. Chem. Soc.* 117: 7285–7286 (1995).

Shioiri et al., "Reaction of Diethyl Phosphorocyanidate(DEPC) with Carboxylic Acids. A New Synthesis of Carboxylic Esters and Amides," *Tetrahedron* 32(18):2211–2217 (1976).

Tung et al., "A New Method for the Preparation of O,O'–Dialkylphosphoryl Cyanides," *Hua Hsueh Hsueh Pao* (*Acta Chimica Sinica*) 31(3): 199–202 (1965).

*Primary Examiner*—Michael G. Ambrose
*Attorney, Agent, or Firm*—James M. Warner; Arnold, White & Durkee

[57] ABSTRACT

A process for preparing cyanophosphonate derivatives involves contacting phosphoric anhydride ($P_4O_{10}$) and a cyanide, preferably in the presence of a Lewis base, in a reaction mixture under sufficient conditions to produce a cyanophosphonate derivative. The cyanophosphonate derivative can be subsequently hydrogenated to produce an aminomethylphosphonate derivative.

48 Claims, No Drawings

METHOD FOR PREPARING CYANOPHOSPHONATE DERIVATIVES FROM PHOSPHORIC ANHYDRIDE AND CYANIDE

This application claims the benefit of provisional application Ser. No. 60/034,512, filed Dec. 30, 1996.

BACKGROUND OF THE INVENTION

Phosphorus-containing compounds such as cyanophosphonate derivatives are important precursors for the synthesis of organophosphorus compounds, which have numerous applications, for example, in herbicides, insecticides, fertilizers, flame retardants and plasticizers. Cyanophosphonate derivatives can be converted to aminomethylphosphonate derivatives, which have been particularly important precursors in the synthesis of N-phosphonomethylglycine, a highly effective commercial herbicide (available under the trade name Roundup™ useful for the control of a large variety of weeds. The syntheses of such organophosphorus compounds have commonly used a halogen derivative of phosphorus as a starting material.

There is a need in the art for alternative processes for preparing cyanophosphonate derivatives and novel cyanophosphonate derivatives to be used in the synthesis of phosphorus species. There is a further need for such novel processes and compounds that are economical and have an improved environmental impact over conventional processes using halogen-containing starting materials.

SUMMARY OF THE INVENTION

This invention relates to a process for preparing cyanophosphonate derivatives. More particularly, the invention is directed to a process that involves contacting phosphoric anhydride ($P_4O_{10}$) and a cyanide, preferably in the presence of a Lewis base, in a reaction mixture under sufficient conditions to produce a cyanophosphonate derivative. The cyanophosphonate derivative can be subsequently hydrogenated to produce an aminomethylphosphonate derivative. In a further preferred embodiment, the cyanophosphonate derivative and the aminomethylphosphonate derivative are used as precursors for the production of N-phosphonomethylglycine.

The processes according to the invention offer significant advantages in that they provide a novel, economic route to synthesize cyanophosphonate derivatives having improved environmental impact over conventional processes using halogen-containing phosphorus starting materials.

DESCRIPTION OF ILLUSTRATIVE EMBODIMENTS

The invention is broadly directed to a process that involves contacting phosphoric anhydride ($P_4O_{10}$) and a cyanide, preferably in the presence of a Lewis base, in a reaction mixture under sufficient conditions to produce a cyanophosphonate derivative. That cyanophosphonate derivative can be subsequently hydrogenated to produce an aminomethylphosphonate derivative. In a further preferred embodiment, the cyanophosphonate and aminomethylphosphonate derivatives are used as precursors for the production of N-phosphonomethylglycine.

In a preferred embodiment, the process according to the invention involves charging a reaction vessel with phosphoric anhydride, optionally with a nonreactive, polar solvent. A Lewis base is then added, preferably in an amount ranging from about 1 to about 10 molar equivalents relative to phosphoric anhydride, more preferably about 2 to about 8 molar equivalents, and most preferably about 3 to about 6 molar equivalents. That mixture is then heated under suitable conditions to dissolve or partially dissolve the phosphoric anhydride, e.g., preferably at a temperature of about 40° C. and for about 10 minutes. Subsequently, a cyanide compound is added, preferably in an amount ranging from about 1 to about 15 molar equivalents relative to phosphoric anhydride, more preferably about 2 to about 10 molar equivalents and most preferably about 3.5 to about 8.5 molar equivalents. This mixture is then heated under suitable conditions to carry out the reaction. The reaction temperature can be between about −20° C. and about 150° C., and is preferably between about 0° C. and about 150° C., and more preferably between about 30° C. and about 90° C. The reaction time preferably ranges from about 0.1 to about 50 hours, more preferably from about 0.5 to about 20 hours and most preferably from about 1 to about 6 hours. The Lewis base and any solvent can subsequently be removed from the product mixture, for example, under reduced pressure. The remaining reside can then be quenched with water, alcohol or buffer to yield one or more cyanophosphonate derivatives. The amount of water, alcohol or buffer added to the reaction mixture in the quenching step is preferably at a least stoichiometric amount and more preferably an excess amount.

Phosphoric anhydride is commercially available, for example, from Aldrich Chemical Co. in assays in excess of 99.99%. Phosphoric anhydride is generally available in the form of a powder and can be added to the reaction mixture in various forms. For example, phosphoric anhydride can be added directly as a powder or as a slurry in a solvent or cosolvent.

The cyanide reagent can be hydrogen cyanide or a cyanide salt that is sufficiently reactive with phosphoric anhydride to produce a cyanophosphonate derivative according to the inventive process. For example, the cyanide salt can be an alkali metal cyanide, an alkaline earth metal cyanide, a tetraaryl phosphonium cyanide, an ammonium cyanide, a tetraalkyl ammonium cyanide, tetraalkyl phosphonium cyanide, a tetraaryl phosphonium cyanide, a trialkyl sulfonium cyanide, a cyanide of a cationic form of an organic amine or mixtures thereof. The cyanide reagent is preferably hydrogen cyanide, potassium cyanide, sodium cyanide, lithium cyanide, silver cyanide, gold cyanide, copper cyanide, tetrabutylammonium cyanide or mixtures thereof. More preferably, the cyanide compound is hydrogen cyanide, potassium cyanide, sodium cyanide, tetrabutylammonium cyanide or mixtures thereof.

The Lewis base is generally any base suitable for promoting the production of the cyanophosphonate derivative according to the inventive process. In a preferred embodiment, the Lewis base is triethylamine, diglyme, 4-isopropylpyridine, dibenzylamine, 4-dimethylaminopyridine, tris[2-(2-methoxyethoxy)ethyl] amine, 4-tert-butylpyridine, 4-(5-nonyl)pyridine, trimethylamine, 1,8-bis(dimethylamino)naphthalene, 4-ethylpyridine, phenanthroline, N,N,N',N'-tetramethylethylenediamine,1,4,7,10,13-pentamethyl-1,4,7, 10,13-pentaazacyclopentadecane, quinuclidine, N-methylpyrrolidine, 1,4-diazobicyclo[2.2.2]octane, 1-butylimidazole, 3-benzylpyridine, 1,5-pentamethylenetetrazole, tris[2(2-methoxyethoxy)ethyl] amine, N,N-dimethylaniline, collidine, N-benzylidine aniline, triphenylphosphine or mixtures thereof. More preferably, the Lewis base is 4-tert-butylpyridine, 4-(5- nonyl)pyridine, quinuclidine or N-methylpyrrolidine. The Lewis base can be added to the reaction mixture in an amount ranging from about 1 to about 10 molar equivalents, more preferably from about 2 to about 8 molar equivalents and most preferably from about 3 to about 6 molar equivalents relative to phosphoric anhydride.

The solvent can be any material which enhances the solubility of the reactants or promotes the formation of the desired products. Preferably the solvent is a polar solvent, for example, a nitrile such as acetonitrile, phenylacetonitrile, adiponitrile, propionitrile, dimethylacetonitrile or mixtures thereof. More preferably, the solvent is acetonitrile, phenylacetonitrile or adiponitrile.

The step of contacting phosphoric anhydride and a cyanide can produce a variety of intermediate products, including those disclosed in the co-pending U.S. patent application Ser. No. 08/996,946, entitled "Cyanophosphorus Compounds and Their Preparation," by Patrick J. Lennon and Sergey G. Vulfson, filed Dec. 23, 1997, which is incorporated by reference. For example, the intermediate products can include one or more dicyanophosphinates, cyanopolyphosphates, tricyanocyclotriphosphonates and/or tetracyanocyclotetraphosphates.

Upon quenching of the intermediate product solution with water or a buffer, the product solution preferably contains a cyanophosphonate derivative of cyanophosphonic acid or a cyanophosphonate monosalt monoacid, such as potassium hydrogen cyanophosphonate, sodium hydrogen cyanophosphonate or lithium hydrogen cyanophosphonate. Upon quenching with an alcohol, the product solution preferably contains a cyanophosphonate derivative of cyanophosphonic acid, a cyanophosphonate monosalt monoester, a cyanophosphonate diester, a cyanophosphonate monoacid monoester, a cyanophosphonate monosalt monoacid or a cyanophosphonate disalt. In a further preferred embodiment, the cyanophosphonate derivative is potassium benzyl cyanophosphonate, potassium methyl cyanophosphonate, potassium ethyl cyanophosphonate, sodium benzyl cyanophosphonate, sodium methyl cyanophosphonate, sodium ethyl cyanophosphonate, disodium cyanophosphonate, dipotassium cyanophosphonate, dilithium cyanophosphonate, bis(2-hydroxyethylammonium) cyanophosphonate, bis(ammonium)cyanophosphonate, bis (isopropylammonium)cyanophosphonate, bis (dimethylammonium)cyanophosphonate, mono (isopropylammonium)cyanophosphonate or bis (trimethylsulfonium)cyanophosphonate.

In another preferred embodiment, the cyanophosphonate derivative is a cyclic cyanophosphonate anhydride, a linear cyanophosphonate anhydride, a mixed linear cyanophosphonate-phosphate anhydride or a mixed cyclic cyanophosphonate-phosphate anhydride. For example, the cyanophosphonate derivative can be monocyanopyrophosphate, dicyanopyrophosphate, dicyanotripolyphosphate, dicyanotetrapolyphosphate, monocyanotetrapolyphosphate, monocyanopentapolyphosphate, cyanophosphate cyclotrimer or cyanophosphate cyclotetramer.

The cyanophosphonate derivative product or products are preferably produced in at least 50% yield with respect to the phosphoric anhydride reagent, more preferably at a 55–95% yield, for example, at a 60–90% yield.

The cyanophosphonate derivatives produced by the inventive process can be used as precursors for producing other organophosphorus species. In a preferred embodiment, the cyanophosphonate derivative product can be hydrogenated to produce an aminomethylphosphonate derivative. The hydrogenation may take place by contacting the cyanophosphonate derivative with hydrogen in the presence of a suitable catalyst under sufficient conditions to produce an aminomethylphosphonate derivative. The cyanophosphonate derivative can be provided alone or in a mixture of compounds, including a product mixture or portion of a product mixture from the reaction of a pyrophosphate or polyphosphate ester and cyanide.

The solvent can be any material that enhances the solubility of reactants or promotes the formation of the desired products. In a preferred embodiment, the solvent is water, acetic acid, an alcohol, dimethylacetamide, an anhydride, e.g., acetic anhydride, an amide, sulfolane or mixtures thereof.

Hydrogen pressure can be maintained at a level suitable for the formation of an aminomethylphosphonate derivative, and consistent with the safety limitations of the experimental system. In a preferred embodiment, the hydrogen pressure is between about 0.25 and 5000 psi, more preferably between about 0.5 and about 3000 psi and most preferably between about 1 and about 1000 psi, for example, between about 25 and about 300 psi.

The catalyst is generally any material effective at catalyzing the formation of aminomethylphosphonate derivatives according to the inventive method. In a preferred embodiment, the catalyst is a transition metal catalyst. For example, the hydrogenation step can use a catalyst of a cobalt-containing compound, a nickel-containing compound, a platinum-containing compound, a palladium-containing compound or a rhodium-containing compound. More preferably, the catalyst is Raney cobalt, Raney nickel, a platinum promoted Raney nickel such as platinum tetrachloride ($PtCl_4$) promoted Raney nickel, platinum on carbon, palladium on carbon or rhodium on carbon. The catalyst can be used at a stoichiometric amount or catalytic amount with respect to the cyanophosphonate derivative. The stoichiometric amount is preferably between about 1 molar equivalent and about 5 molar equivalents with respect to the cyanophosphonate derivative, and more preferably between about 1 molar equivalent and about 2 molar equivalents with respect to the cyanophosphonate derivative. The catalytic amount is preferably between about 0.1 molar percent and about 100 molar percent with respect to the cyanophosphonate derivative, and more preferably between about 0.5 molar percent and about 50 molar percent with respect to the cyanophosphonate derivative.

In the event that a catalyst of platinum on carbon, palladium on carbon or rhodium on carbon is used, the hydrogenation reaction mixture preferably further contains an acid in an amount sufficient to promote formation of the desired product. The acid can be an inorganic acid or an organic acid. The inorganic acid is preferably hydrochloric acid, sulfuric acid, phosphoric acid, nitric acid or hydrocyanic acid and, more preferably, is hydrochloric acid. The organic acid is preferably acetic acid, trifluoroacetic acid, trifluoromethanesulfonic acid or p-toluenesulfonic acid. The acid is preferably added to the hydrogenation reaction mixture at a concentration between about 0.1 and 5 molar equivalents with respect to the cyanophosphonate derivative, more preferably at a concentration between about 0.5 and about 2.5 molar equivalents with respect to the cyanophosphonate derivative, and most preferably at a concentration of about 1 molar equivalent or about 2 molar equivalents with respect to the cyanophosphonate derivative, depending on the nature of the cyanophosphonate derivative.

In a preferred embodiment the reaction product mixture from the hydrogenation step is heated under sufficient conditions to further promote the formation of the aminomethylphosphonate derivative. For example, a product mixture that has been partially or substantially hydrogenated can be heated to a temperature in the range of about 135° C. to about 200° C., and more preferably to a range of about 135° C. to about 160° C. This heating step may be conducted for any amount of time that further promotes the aminomethylphosphonate derivative formation, preferably about 1 to about 12 hours. The heating time for optimum aminomethylphosphonate derivative formation can depend on the pH and the nature of the cations in the reaction mixture.

The products of the hydrogenation step can be isolated from the reaction mixture by conventional methods or can be used for some purposes without isolation from the reaction product mixture. Further details regarding cyanophosphonate derivative hydrogenation are provided in co-pending U.S. application Ser. No. 08/996,948, entitled "Method for Preparing Aminomethylphosphonate Derivatives Via Hydrogenation of Cyanophosphonate Derivatives," by Patrick J. Lennon, filed Dec. 23, 1997, which is incorporated herein by reference.

The aminomethylphosphonate derivative product of the inventive process can be used as a precursor for producing other organophosphorus species. In a preferred embodiment, aminomethylphosphonic acid can used for producing N-phosphonomethylglycine. Methods for producing N-phosphonomethylglycine from aminomethylphosphonic acid are disclosed, for example, in U.S. Pat. No. 4,221,583 (Monsanto Co.), which is incorporated herein by reference.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Preparation of Cyanophosphonate Derivatives from Phosphoric Anhydride and Cyanides for NMR Analysis Preparation 1

Under inert atmosphere, 0.07 g (0.25 mol) of $P_4O_{10}$ was mixed with 1 ml of dry $CH_3CN$ and 0.10 g (1.0 mmol) of triethylamine were added. The mixture was then heated at 40° C. for 5 minutes, after that 0.07 g (1.06 mmol) of KCN were added to this solution. The solid KCN was crushed with a spatula around the walls of the glass vial under the surface of the reaction mixture. The mixture was heated at 40° C. overnight. After removal of the solvent under reduced pressure, the resulting powder was dissolved in $D_2O$ and the NMR spectra were recorded. The pH was adjusted as needed by the addition of acid or base.

Preparation 1a

The reaction was carried out according to the procedure in Example 1 using the same molar quantities of reagents, except that $K^{13}CN$ was used instead of $K^{12}CN$.

Preparation 2

Under inert atmosphere, 0.07 g (0.25 mol) of $P_4O_{10}$ was mixed with 1 ml of dry $CH_3CN$ and 0.135 g (1.0 mmol) of 4-tert-butylpyridine were added. The mixture was then heated at 40° C. for 5 minutes, after that 0.07 g (1.06 mmol) of KCN were added to this solution. The solid KCN was crushed with a spatula around the walls of the glass vial under the surface of the reaction mixture. The mixture was heated at 40° C. overnight. After removal of the solvent under reduced pressure, the resulting powder was dissolved in $D_2O$ and the NMR spectra were recorded. The pH was adjusted as needed by the addition of acid or base.

Preparation 3

Under inert atmosphere, 0.07 g (0.25 mol) of $P_4O_{10}$ was mixed with 1 ml of dry $CH_3CN$ and 0.10 g (1.0 mmol) of triethylamine were added. The mixture was then heated at 40° C. for 5 minutes, after that 0.269 g (1.0 mmol) of $(C_4H_9)_4NCN$ were added to this solution. The mixture was heated at 40° C. overnight. A small quantity of dry $CD_3CN$ was added to the solution before the NMR spectra were run.

The product mixtures for Preparations 1, 1A, 2 and 3 were then evaluated by NMR, the results of which are summarized in Tables I–VI.

| Molecule ID | Assignment | Formula |
|---|---|---|
| Species Assignment Key for Tables I–IV, VI | | |
| A | Cyclic trimer or tetramer | $(CN)_3(PO_2)_3$ or $(CN)_4(PO_2)_4$ |
| B | Symmetrical linear trimer | $[NCPO_3PO_3PO_2CN]^{3-}$ |
| C | Symmetrical linear tetramer | $[NCPO_3PO_3PO_3PO_2CN]^{4-}$ |
| D | Unsymmetrical linear tetramer | $[NCPO_3PO_3PO_3PO_3]^{5-}$ |
| E | Unsymmetrical linear pentamer | $[NCPO_3PO_3PO_3PO_3PO_3]^{6-}$ |
| L | Cyanophosphonate (monomer A) | $[NCPO_3]^{2-}$ |
| Table V | | |
| 1 | Dicyanophosphinate (monomer B) | $[(NC)_2PO_2]^{1-}$ |
| 12 | Cyclic trimer or tetramer | $(CN)_3(PO_2)_3$ or $(CN)_4(PO_2)_4$ |

TABLE I $^{31}P$ NMR Data for Preparation 1 (pH ~2.5, 3 day solution)

| Molecule ID | Approx. % | Highest Field Pattern Chemical Shift (ppm) $J_{pp}$ (Hz) | Coupled Partner Pattern Chemical Shift (ppm) $J_{pp}$ (Hz) |
|---|---|---|---|
| A | 25.3 | S −33.69 | |

TABLE I-continued

$^{31}$P NMR Data for Preparation 1 (pH ~2.5, 3 day solution)

| Molecule ID | Approx. % | Highest Field Pattern Chemical Shift (ppm) $J_{pp}$ (Hz) | Coupled Partner Pattern Chemical Shift (ppm) $J_{pp}$ (Hz) | | | |
|---|---|---|---|---|---|---|
| B | 10.0 | D<br>−33.02<br>20.9 | T<br>−23.63<br>20.9 | | | |
| C | 3.9 | HOP<br>−32.6 | HOP<br>−22.9 | | | |
| D | 3.4 | D<br>−32.42<br>18.9 | DD<br>−22.43<br>18.8 | HOP<br>−22.27 | HOP<br>−21.77 | |
| E | 9.5 | D<br>−32.38<br>19.3 | DD<br>−22.21<br>19.2, 16.8 | DD<br>−21.56 | HOP<br>−21.1 aprox | HOP<br>−20.9 aprox |
| F | <1 | D<br>−32.17<br>20.9 | D<br>−9.83<br>20.7 | | | |
| G | <1 | D<br>−31.54<br>12.3 | partner not located | | | |
| H | 2.1 | S<br>−22.36 | | | | |
| I | <1 | S<br>−22.51 | | | | |
| J | 3.2 | D<br>−21.37<br>15.3 | O<br>−9.49<br>O | | | |
| K | 6.2 | S<br>−20.25 | | | | |
| L | 35.6 | S<br>−14.38 | | | | |
| M | <1 | S<br>−1.13 | | | | |

S = singlet
T = triplet
DD = doublet of doublets
D = doublets
HOP = higher order pattern
O = obscured

TABLE II

$^{31}$P NMR Data for Preparation 1 (pH = 8.2, 1 hr solution)

| Molecule ID | Approx. % | Highest Field Pattern Chemical Shift (ppm) $J_{p-p}$ (Hz) | Coupled Partners Pattern Chemical Shift (ppm) $J_{pp}$ (Hz) | | | |
|---|---|---|---|---|---|---|
| A | 28.9 | S<br>−33.64 | | | | |
| B | 12.4 | D<br>−33.90<br>20.9 | T<br>−23.50<br>20.9 | | | |
| C | 4.9 | HOP<br>−32.47 | HOP<br>−22.73 | | | |
| D | 3.8 | D<br>−32.31<br>18.7 | DD<br>−22.27<br>18.3 | HOP<br>−21.09 | | |
| E | 11.7 | D<br>−32.27<br>19.3 | DD<br>−22.05<br>19.1, 16.9 | DD<br>−21.39<br>16.3, 15.3 | HOP<br>−20.74 | HOP<br>−20.74 |
| $^2$X | <1 | D<br>−31.50<br>12.90 | TOSCY sw did not include coupled portion | | | |
| $^2$Y | <1 | D<br>−30.53<br>22.66 | TOSCY sw did not include coupled portion | | | |
| H | 1.1 | S<br>−22.44 | | | | |
| I | 1.2 | S<br>−22.21 | | | | |

TABLE II-continued

$^{31}$P NMR Data for Preparation 1 (pH = 8.2, 1 hr solution)

| Molecule ID | Approx. % | Highest Field Pattern Chemical Shift (ppm) $J_{p-p}$ (Hz) | Coupled Partners Pattern Chemical Shift (ppm) $J_{PP}$ (Hz) |
|---|---|---|---|
| J | 7.6 | D<br>−21.20<br>14.8 | TOSCY sw did not include coupled portion |
| K | 26.5 | S<br>−20.14 | |
| L | | S<br>−14.25 | |

S = singlet
HOP = higher order pattern
D = doublet
DD = doublet of doublets
T = triplet
SW = sweep width
[2]X and Y may be identical to F and G (Table I) but shifts are notably different.

TABLE III

$^{31}$P NMR Data for Preparation 2 (pH = 3.2, 24 hr solution)

| Molecule ID | Approx. % | Highest Field Pattern Chemical Shift (ppm) $J_{p-p}$ (Hz) | Coupled Partners Pattern Chemical Shift (ppm) $J_{PP}$ (Hz) | | | |
|---|---|---|---|---|---|---|
| A | 39.2 | S<br>−33.75 | | | | |
| B | 6.6 | D<br>−33.05<br>20.9 | T<br>−23.66<br>20.9 | | | |
| C | 2.5 | HOP<br>−32.64 | HOP<br>−22.92 | | | |
| D | <1 | D<br>−32.47<br>19.3 | DD<br>−22.24 | HOP<br>−21.28 | HOP<br>−21.78 | |
| E | 6.0 | D<br>−32.43<br>19.3 | DD<br>22.24 | DD<br>−21.60 | HOP<br>−21.16 | HOP<br>−20.95 |
| F | 9.5 | D<br>−32.19<br>21.1 | −9.81<br>21.1 | | | |
| G | | Absent | | | | |
| H | <1 | S<br>−22.65 | | | | |
| I | 1.4 | S<br>−22.39 | | | | |
| J | 2.6 | D<br>−21.46 | O<br>−9.46 | | | |
| K | 5.4 | S<br>−20.30 | | | | |
| L | 23.4 | S<br>−15.67 | | | | |
| M | 1.0 | S<br>+1.13 | | | | |
| N | <1 | S<br>−21.82 | | | | |

S = singlet
DD = doublet of doublets
D = doublet
O = obscured
T = triplet
HOP = higher order pattern

TABLE IV $^{31}P-^{13}C$ Coupling Constants from Preparation 1a

| Molecule ID | $J_{P-C}$ coupling constant in hertz |
|---|---|
| A | $^1J_{PC}$ = 204.7 Hz    $^3J_{PC}$ = 11.04 Hz |
| B | 200.5 Hz |
| C | 199.9 Hz |
| D | 199.2 Hz |
| E | 198.9 Hz |
| L | 157.3 Hz |

TABLE V

Chemical shifts and coupling constants for
P containing molecular species in Preparation 3

| Molecule ID | Approx % | Pattern Chem Shift (ppm) $J_{p-p}$ (Hz) | Coupled Partner(s) |
|---|---|---|---|
| 1 | 16.8 | S −47.36 | |
| 2 | <1 | T −37.68 24.5 | peak at −19.47 observed by #18 |
| 3 | <1 | Q −34.90 22.7 | #7 |
| 4 | <1 | S −33.62 | |
| 5 | <1 | S −33.44 | |
| 6 | <1 | DX −32.92 25.88 | 6A |
| 7 | 2.1 | S −32.75 23 | #3 |
| 8 | 1.7 | M −32.55 | 15, 16 |
| 9 | <1 | D −21.82 | CNL |
| 10 | <1 | D −32.18 | CNL |
| 11 | 7.2 | D −31.8 19.1 | 13, 18 |
| 12 | 9.2 | S −30.9 | |
| 13 | 7.3 | HOP 29.86 | 11,18 |
| 14 | 20.4 | D −29.71 20.6 | 17 |
| 15 | 1.4 | HOP −22,32 | 8,16 |
| 16 | <1 | T −21.48 24.0 | 15,8 |
| 17 | 10 | T 20.28 21.05 | 14 |
| 18 | 16 | D −19.54 22.6 | 11,13 |
| 19 | 3 | D −19.08 22.5 | obscured peak at 30.2 ppm |
| 20 | <1 | D −18.11 22.5 | obscured peak at 29.5 |

TABLE V-continued

Chemical shifts and coupling constants for
P containing molecular species in Preparation 3

| Molecule ID | Approx % | Pattern Chem Shift (ppm) $J_{p-p}$ (Hz) | Coupled Partner(s) |
|---|---|---|---|
| 6A | <1 | D −31.17 25.88 | 6 |

S = singlet
D = doublet
T = triplet
Q = quartet
HOP = higher order pattern
CNL = cannot locate

TABLE VI $^{13}C$ Chemical Shifts and C–P Coupling Constants for
CN Containing Species in Preparation 1a with
Triethylamine Base (5 day solution)

| Molecule ID | Approx. % | $^{13}C$ Chemical Shift[a] (ppm) | $^1J_{CP}$ Hz | $^3J_{CP}$ Hz |
|---|---|---|---|---|
| A | 12.3 | 116.34 | 204.7 | 11.0 |
| B | 7.1 | 116.80 | 200.5 | |
| C | 3.8 | 117.01 | 199.9 | |
| D | 2.9 | 117.09 | 199.2 | |
| E | 5.5 | 117.10 | 198.9 | |
| [b]F | 1.2 | 117.10 | 196.2 | |
| [b]G | <1 | 117.40 | 174.4 | |
| L | 35.0 | 119.71 | [c]166.7 | |
| O | 31.6 | 110.80 | | |

[a]referenced to $\underline{C}H_3CN$ at 118.2 ppm
[b]assignment speculative
[c]this $^1J_{CP}$ is time dependent

General Procedure for Examples 2–6

Under an inert atmosphere, 1 molar part of $P_4O_{10}$ was mixed with dry polar solvent ($CH_3CN$ is preferred, 4 ml per mmol $P_4O_{10}$) and four molar parts of dry Lewis base were added. The mixture was then heated at 40° C. to effect partial or total dissolution of $P_4O_{10}$ (about 5–10 minutes), after which 4.3 molar parts of $K^{13}CN$ were added to this solution. The solid KCN was crushed with a spatula around the walls of the glass vessel, e.g., a glass vial, under the surface of the reaction mixture. The mixture was heated at the specified temperature, usually between 40°–80° C., for the specified time period, often between 2–20 hours. At the end of this time period, the solvent and organic base were removed using a vacuum pump. The solid residue contained one or more cyanophosphonate derivatives and was hydrolyzed by water or buffer, thereby yielding cyanophosphonate derivatives.

Example 2

The reaction was carried out in 4 ml of $CH_3CN$ with $P_4O_{10}$ (0.28 g, 0.986 mmol), 4-tert-butylpyridine (0.54 g, 4 mmol) and $K^{13}CN$ (0.28 g, 4.234 mmol) at 48° C. for 20 hours. The solvent and part of the 4-tert-butylpyridine were removed (oil pump, 40° C., for 2 hours). The solid residue was hydrolyzed in water or buffer at pH=2, yielding 87.4% or 86.5% of cyanophosphonate derivatives, respectively. Several products with P—C bonds are evident from the large coupling constants (>140 Hz) in the region around −35 ppm, as well as cyanophosphonate in the −18 to −20 ppm region as a doublet ($^1J_{PC}$=146.6 Hz). On standing, the amount of the latter product increased.

Example 3

The reaction was carried out in 1 ml of $CH_3CN$ with $P_4O_{10}$ (0.07 g, 0.25 mmol), 4-tert-butylpyridine (0.135 g, 1.0 mmol), and $K^{13}CN$ (0.07 g, 1.06 mmol) at 80° C. for 2 hours. $CH_3CN$ and part of the 4-tert-butylpyridine were removed (oil pump). The residue was hydrolyzed by water, and two layers were formed. The top (organic) layer was extracted by $CH_2Cl_2$ and showed no significant signals in the $^{31}P$ NMR spectrum. According to $^{31}P$ NMR, the bottom (water) layer contained 83% cyanophosphonate derivatives.

Example 4

This reaction was carried out in 1 ml of $CH_3CN$ with $P_4O_{10}$ (0.07 g, 0.25 mmol), 4-(5-nonyl)pyridine (0.21 g, 1.02 mmol) and $K^{13}CN$ (0.07 g, 1.06 mmol) at 48° C. for 16 hours (overnight), then at 80° C. for 1 hour. The solvent was removed under reduced pressure, and the residue was hydrolyzed with water producing two layers. The top (organic) layer, diluted with methanol, contained only two signals in the $^{31}P$ NMR spectrum corresponding to cyanophosphonate derivatives, one of which was cyanophosphonate. The bottom (water) layer yielded 84.5% of cyanophosphonate derivatives with cyanophosphonate accounting for 24%.

Example 5

The reaction was carried out in 1 ml of $CH_3CN$ with $P_4O_{10}$ (0.07 g, 0.25 mmol), triethylamine (0.10 g, 1.0 mmol) and $K^{13}CN$ (0.07 g, 1.06 mmol) at 80° C. for 1 hour. The solvent and amine were removed under reduced pressure. The solid residue was hydrolyzed with water yielding 63% of cyanophosphonate derivatives (23% as cyanophosphonate).

Example 6

In dry acetonitrile (7 ml), $P_4O_{10}$ (0.5 g, 1.76 mmol), triethylamine (0.7 g, 6.9 mmol) and $K^{13}CN$ (0.5 g, 7.56 mmol) were combined and heated at 40° C. for 16 hours. Then the solvent and triethylamine were removed under reduced pressure. The solid residue was hydrolyzed with water yielding 64% of cyanophosphonate derivatives (32% as cyanophosphonate; the remainder as compounds with chemical shifts in the range −31.5 to −34.9 ppm (large doublets of varying multiplicities)) in the $^{31}P$ NMR spectrum.

TABLE VII

Reactions of $P_4O_{10}$ and Cyanide

| CN Cation | Base | Ratio of Molar Equiv. $P_4O_{10}$CN | Ratio of Molar Equiv. $P_4O_{10}$Base | Solvent | Additive | Temp | Time (hr) | PCN[1] % | $H_2O$[2] Time | Comments |
|---|---|---|---|---|---|---|---|---|---|---|
| K+ | 4-t-butylpyridine | 1:4 | 1:4 | $CH_3CN$ | | 48° C. | 20 | 84<br>85<br>81 | <1 h<br>17 h<br>73 h | $K^{13}CN$ was powdered in react. mixture, buffer w pH = 4.0 |
| K+ | 4-t-butylpyridine | 1:4 | 1:4 | $CH_3CN$ | | 48° C. | 20 | 87<br>69 | <1 h<br>73 h | $K^{13}CN$ was powdered in react. mixture, $H_2O$ |
| K+ | 4-t-butylpyridine | 1:4 | 1:4 | $CH_3CN$ | | 48° C. | 2.0 | 87<br>64 | <1 h<br>73 h | $K^{13}CN$ was powdered in react. mixture, buffer w pH = 2.0 |
| K+ | 4-t-butylpyridine | 1:4 | 1:4 | $CH_3CN$ | | 48° C. | 20 | 86<br>80 | <1 h<br>73 h | $K^{13}CN$ was powdered in react. mixture, buffer w pH = 5.0 |
| K+ | 4-t-butylpyridine | 1:4 | 1:4 | $CH_3CN$ | | 48° C. | 20 | 86<br>78 | <1 h<br>73 h | $K^{13}CN$ was powdered in react. mixture, buffer w pH = 10.0 |
| K+ | 4-t-butylpyridine | 1:4 | 1:4 | $CH_3CN$ | | 48° C. | 20 | 85<br>80 | <1 h<br>73 h | $K^{13}CN$ was powdered in react. mixture, buffer w pH = 12.0 |
| K+ | 4-t-butylpyridine | 1:4 | 1:4 | $CH_3CN$ | | 48° C. | 20 | 84<br>74 | <1 h<br>73 h | $K^{13}CN$ was powdered in react. mixture, buffer w pH = 8.0 |
| K+ | 4-t-butylpyridine | 1:4 | 1:4 | $CH_3CN$ | | 48° C. | 20 | 84<br>73 | <1 h<br>73 h | $K^{13}CN$ was powdered in react. mixture, buffer w pH = 6.0 |
| K+ | 4-t-butylpyridine | 1:4 | 1:4 | $CH_3CN$ | | 48° C. | 20 | 84<br>67 | <1 h<br>73 h | $K^{13}CN$ was powdered in react. mixture, buffer w pH = 7.0 |
| K+ | 4-t-butylpyridine | 1:8 | 1:4 | $CH_3CN$ | | 40° C. | 16 | 60<br>60 | <1 h | $K^{13}CN$, $D_2O$ |
| K+ | triethylamine | 1:4 | 1:4 | $CH_3CN$ | | 40° C. | 16 | 56<br>53 | <1 h<br>25 h | $K^{13}CN$, $D_2O$ |
| K+ | triethylamine | 1:8 | 1:4 | $CH_3CN$ | | 40° C. | 16 | 55<br>53 | <1 h<br>25 h | $K^{13}CN$, $D_2O$ |
| K+ | triethylamine | 1:2 | 1:4 | $CH_3CN$ | | 40° C. | 16 | 46<br>44 | <1 h<br>25 h | $K^{13}CN$, $D_2O$ |
| K+ | N,N,N',N'-tetramethyl ethylenediamine | 1:4 | 1:4 | $CH_3CN$ | | 40° C. | 7 | 18<br>19 | <1 h<br>17 h | $K^{13}CN$, $D_2O$ |
| K+ | 4-t-butylpyridine | 1:4 | 1:4 | $CH_3CN$ | | 48° C.<br>+80° C. | 16 + 1 | 89 | <1 h | $K^{13}CN$ was powdered in react. mixture, buffer w pH = 2.0 |
| K+ | 4-t-butylpyridine | 1:4 | 1:4 | $CH_3CN$ | | 52° C. | 17 | 86 | <1 h | $K^{13}CN$ was powdered in react. mixture, $H_2O$ |
| K+ | 4-(5-nonyl)-pyridine | 1:4 | 1:4 | $CH_3CN$ | | 48° C.<br>+80° C. | 16 + 1 | 85 | <1 h | $K^{13}CN$ was powdered in react. mixture, buffer w pH = 2.0 |
| K+ | 4-t-butylpyridine | 1:5 | 1:5 | $CH_3CN$ | | 78° C. | 2.75 | 84 | <1 h | $K^{13}CN$ was powdered in react. mixture, $D_2O$ pH = 5.5 |
| K+ | 4-t-butylpyridine | 1:4 | 1:4 | $CH_3CN$ | | 80° C. | 2 | 82 | <1 h | $K^{13}CN$ was powdered in react. mixture, $D_2O$ pH = 5.9 |
| K+ | 4-t-butylpyridine | 1:4 | 1:4 | $CH_3CN$ | | 80° C.<br>+40° C. | 1.5+1 | 82 | <1 h | $K^{13}CN$ was powdered in react. mixture, $D_2O$ |
| K+ | 4-(5-nonyl)-pyridine | 1:4 | 1:4 | BzCN + CH3CN | | 50° C.<br>+85° C. | 20 + | 79 | <1 h | $K^{13}CN$ was powdered in react. mixture, $H_2O$ |

TABLE VII-continued

Reactions of P₄O₁₀ and Cyanide

| CN Cation | Base | Ratio of Molar Equiv. P₄O₁₀:CN | Ratio of Molar Equiv. P₄O₁₀:Base | Solvent | Additive | Temp | Time (hr) | PCN[1] % | H₂O[2] Time | Comments |
|---|---|---|---|---|---|---|---|---|---|---|
| K+ | Me₅[15]aneN₅ | 1:4 | 1:4 | CH₃CN | | 50° C. | 16 | 78 | | K¹³CN was powdered in react. mixture, D₂O pH = 9.45 |
| K+ | quinuclidine | 1:4 | 1:4 | CH₃CN | | 48° C. +80° C. | 16 + 1 | 77 | <1 h | K¹³CN was powdered in react. mixture, D₂O |
| K+ | 4-t-butylpyridine | 1:4 | 1:4 | CH₃CN | | 80° C. +50° C. | 1+24 | 75 | <1 h | K¹³CN was powdered in react. mixture, buffer w pH = 2.0 |
| K+ | 4-benzylpyridine | 1:4 | 1:4 | CH₃CN | | 50° C. | 16 | 73 | <1 h mixture, buffer w pH = 2.0 | K¹³CN was powdered in react. |
| K+ | 4-t-butylpyridine | 1:4 | 1:4 | CH₃CN | | 45° C. | 72 | 71 | <1 h | K¹³CN was powdered in react. mixture, buffer w pH = 2.0 |
| K+ | 4-(5-nonyl)-pyridine | 1:4 | 1:4 | adipoCN | | 80° C. | 3 | 70 | <1 h | K¹³CN, D₂O |
| K+ | 4-t-butylpyridine | 1:4 | 1:4 | BzCN + CH₃CN | | 50° C. +85° C. | 20 + 1 | 67 | <1 h | K¹³CN was powdered in react. mixture, H₂O |
| K+ | 4-t-butylpyridine | 1:4 | 1:2 | CH₃CN | | 80° C. | 2 | 66 | <1 h | K¹³CN was powdered in react. mix, buffer pH = 6.0 pH = 2.9 (real) |
| K+ | 4-t-butylpyridine | 1:4 | 1:2 | CH₃CN | | 80° C. | 2 | 65 | <1 h | K¹³CN was powdered in react. mix, buffer pH = 6.0 pH = 29(real) |
| K+ | triethylamine | 1:4 | 1:4 | CH₃CN | | 40° C. | 16 | 64 | <1 h | K¹³CN was powdered in react. mixture, D₂O |
| K+ | 1,4-diazabicyclo [2.2.2]octane | 1:4 | 1:4 | CH₃CN | | 40° C. | 16 | 63 | <1 h | K¹³CN was powdered in react. mixture, D₂O pH = 8.1 |
| K+ | triethylamine | 1:4 | 1:4 | CH₃CN | | 80° C. | 1 | 63 | <1 h | K¹³CN was powdered in rect. mixture, D₂O pH = 7.8 |
| K+ | 4-t-butylpyridine | 1:4 | 1:4 | sulfolane | | 85° C. +50° C. | 724 24 | 63 | <1 h | K¹³CN was powdered in react. mixture, buffer w pH = 2.0 |
| K+ | 4-t-butylpyridine | 1:4 | 1:2 | CH₃CN | | 80° C. | 2 | 62 | <1 h | K¹³CN was powdered in react. mix, D₂O pH = 2.4 |
| K+ | 4-t-butylpyridine | 1:4 | 1:2 | CH₃CN | | 80° C. | 2 | 62 | <1 h | K¹³CN was powdered in react. mixture, D₂O +K₂CO₃ pH = 10.1 |
| K+ | 4-t-butylpyridine | 1:4 | 1:4 | CH₃CN | | 87° C. | 0.25 | 61 | <1 h | K¹³CN was powdered in react. mixture, D₂O pH = 3.85 |
| K+ | triethylamine | 1:4 | 1:4 | CH₃CN | | 40° C. | 7 | 59 | <1 h | K¹³CN, D₂O |
| K+ | 1-butylimidazole | 1:4 | 1:4 | CH₃CN | | 48° C. +80° C. | 16+1 | 59 | <1 h | K¹³CN, D₂O |
| K+ | 4-benzylpyridine | 1:4 | 1:4 | CH₃CN | | 40° C. | 16 | 59 | <1 h | K¹³CN was powdered, dried oil pump 80° C., 24h. D₂O |
| 4 NBu₄+ +2K+ | triethylamine | 1:4 + 2 | 1:4 | CH₃CN | DMSO | 50° C. | 16 | 58 | <1 h | K¹³CN was powdered in react. mixture, buffer w pH = 2.0 |
| K+ | triethylamine | 1:4 | 1:4 | CH₃CN | 2 eq. Zn(CN)₂ | 40° C. | 16 | 57 | | K¹³CN was added in 2h; polymer or gel, DMSO was added with KCN D₂O |

TABLE VII-continued

Reactions of P$_4$O$_{10}$ and Cyanide

| CN Cation | Base | Ratio of Molar Equiv. P$_4$O$_{10}$:CN | Ratio of Molar Equiv. P$_4$O$_{10}$:Base | Solvent | Additive | Temp | Time (hr) | PCN[1] % | H$_2$O[2] Time | Comments |
|---|---|---|---|---|---|---|---|---|---|---|
| K$^+$ | triethylamine | 1:8 | 1:8 | CH$_3$CN | | 40° C. | 16 | 57 | <1 h | buffer pH = 7.4 |
| K$^+$ | 3-benzylpyridine | 1:4 | 1:4 | CH$_3$CN | | 50° C. | 16 | 55 | <1 h | K$^{13}$CN was powdered in react. mixture, H$_2$O |
| K$^+$ | triethylamine | 1:4 | 1:4 | CH$_3$CN | | 40° C. | 16 | 54 | <1 h | K$^{13}$CN, D$_2$O |
| 4 NBu$_4^+$ + 2K$^+$ | triethylamine | 1:4 + 2 | 1:4 | CH$_3$CN | 1.1 eq Bu$_4$NI dimethyl formamide | 40° C. | 16 + 2 | 54 | <1 h | K$^{13}$13CN was added in 16 h Only PCN before hydrolysis DMF was added with KCN |
| K$^+$ | tributylamine | 1:4 | 1:4 | CH$_3$CN | | 50° C. | 16 | 53 | <1 h | K$^{13}$CN was powdered in react. mixture, D$_2$O pH = 4.03 |
| K$^+$ | 1,5-penta methylene tetrazole | 1:4 | 1:4 | CH$_3$CN | | 50° C. | 16 | 52 | <1 h | K$^{13}$CN was powdered under CH$_3$CN; D$_2$O pH = 9.6 |
| 4 NBu$_4^+$ + 4K$^+$ | triethylamine | 1:1 + 4 | 1:4 | CH$_3$CN | | 40° C. | 2+2 | 52 | <#h | K$^{13}$CN was added in 2h; polymt or gel, after hydrolysis by H$_2$O pH = 9.1 |
| K$^+$ | 4-t-butylpyridine | 1:4 | 1:4 | BzCN | | 50° C. | 24 | 52 | <1 h | K$^{13}$CN was powdered in react. mixture, H$_2$O |
| 4 NBu$_4^+$ + 2K$^+$ | triethylamine | 1:4 + 2 | 1:4 | CH$_3$CN | | 50° C. | 16+2 | 51 | <1 h | K$^{13}$CNwas added in 16 h Only PCN before hydrolysis, though gel is possible |
| 4Na$^+$ | triethylamine | 1:4 | 1:4 | CH$_3$CN | 4eq 5-crown-15 | 40° C. | 1 | 51 | <1 h | buffer pH = 7.4 |
| K$^+$ | tributylamine | 1:8 | 1:4 | CH$_3$CN | | 40° C. | 48 | 50 | <1 h | K$^{13}$ CN, D$_2$O |
| K$^+$ | tris[2(2-methoxy ethoxy)ethyl]amine | 1:8 | 1:4 | CH$_3$CN | | 40° C. | 16 | 49 | <1 h | K$^{13}$ CN, D$_2$O |
| 4 NBu$_4^+$ + 4K$^+$ | triethylamine | 1:2 + 4 | 1:4 | CH$_3$CN | | 40° C. | 2+2 | 47 | <1 h | K$^{13}$ CN was added in 2h; polym( or gel, after hydrolysis by H$_2$O pH = 9.4 |
| K$^+$ | diglyme | 1:4 | 1:4 | CH$_3$CN | 4HCl -dioxane | 40° C. | 16 | 46 | <1 h | K$^{13}$ CN,D$_2$O |
| NBu$_4^+$ | triethylamine | 1:4 | 1:4 | CH$_3$CN | | 40° C. | 16 | 44 | K$^{13}$CN, D$_2$O | <1 h | |
| K$^+$ | N,N-dimethyl aniline | 1:8 | 1:4 | CH$_3$CN | 40° C. | 48 | 42 | | <1 h | |
| 4K$^+$ | diglyme | 1:4 | 1:4 | CH$_3$CN | | 40° C. | 16. | 40 | <1 h | |
| K$^+$ | tributylamine | 1:8 | 1:4 | CH$_3$CN | Cap(C$_8$H$_{17}$)$_3$ MeNCl | 40° C. | 16 | 40 | <1 h | K$^{13}$CN, D$_2$O |
| 4K$^+$ | triethylamine | 1:4 | 1:4 | adipoCN | | 80° C. | 16 | 39 | <1 h | buffer pH = 7.4. |
| K$^+$ | triethylamine | 1:8 | 1:4 | CH$_3$CN | | 82° C. | 72 | 38 | <1 h | K$^{13}$CN, D$_2$O |
| 2K$^+$ + 3 NBu$_4^+$ | triethylamine | 1:5 | 1:4 | CH$_3$CN | | 40° C. | 16 | 37 | <1 h | Mixt. K$^+$ + NBu$^+$was used, there is precipitate |
| K$^+$ | collidine | 1:8 | 1:4 | CH$_3$CN | | 40° C. | 24 | 37 | <1 h | K$^{13}$ CN, D$_2$O |
| K$^+$ | tribenzylamine | 1:4 | 1:4 | CH$_3$CN | | 50° C. | 16 | 37 | <1 h | K$^{13}$ CN was powdered in react. mixture, H$_2$O |

TABLE VII-continued

Reactions of $P_4O_{10}$ and Cyanide

| CN Cation | Base | Ratio of Molar Equiv. $P_4O_{10}$:CN | Ratio of Molar Equiv. $P_4O_{10}$:Base | Solvent | Additive | Temp | Time (hr) | PCN[1] % | $H_2O^2$ Time | Comments |
|---|---|---|---|---|---|---|---|---|---|---|
| K+ | none | 1:4 | 1:4 | CH₃CN | | 40° C. | 72 | 37 | <1 h | K[13] CN was powdered in react mixture, H₂O |
| K+ | triethylamine | 1:4 | 1:4 | CH₃CN | 0.15LaCl₃ | 40° C. | 16 | 36 | <1 h | K[13] CN, D₂O |
| K+ | triethylamine | 1:4 | 1:4 | CH₃CN | 4 HCl-dioxane | 40° C. | 16 | 35 | <1 h | K[13] CN, D₂O pH = 8.34 |
| K+ | N-benzylidine aniline | 1:4 | 1:4 | CH₃CN | | 50° C. | 16 | 35 | <1 h | K[13] CN was powdered in react mix., buffer pH = 2.0 pH = 4 03 |
| K+ | isoquinoline | 1:4 | 1:4 | CH₃CN | | 40° C. | 16 | 27 | <1 h | K[13] CN was powdered in react mix., D₂O |
| K+ | tris[2(2-methoxy ethoxy)ethyl]amine | 1:4 | 1:4 | CH₃CN | | 40° C. | 16 | 26 | <1 h | K12CN, D2Q |
| K+ | triethylamine | 1:4 | 1:4 | CH₃CN | 1eq. Pd(CN)₂ | 40° C. | 16 | 25 | <1h | K—CN, D₂O |
| K+ | 1,3,5-tribenzyl hexahydro-1,3,5-triazine | 1:8 | 1:0 | CH₃CN | | 40° C. | 72 | 24 | <1 h | K[13] CN,D₂O |
| K+ | | 1:4 | 1:4 | CH₃CN | | 50° C. | 16 | 24 | <1 h | K[13]CN was powdered in react. mixture,H₂O |
| K+ | 1,8-diazabicyclo [5.4.0]undec-7-ene | 1:4 | 1:4 | CH₃CN | | 40° C. | 16 | 23 | <1 h | K[13] CN, D₂O pH = 10.0 |
| K+ | 1,5-diazabicyclo [5.4.0]undec-7-ene | 1:4 | 1:4 | CH₃CN | | 40° C. | 16 | 22 | <1 h | K[13] CN, D₂O pH = 10.0 |
| K+ | triphenyl phosphine | 1:4 | 1:4 | CH₃CN | | 50° C. | 16 | 16 | <1 h | K[13] CN was powdered in react. mixture, H₂O |
| K+ | 4-dimethylamino pyridine | 1:8 | 1:4 | CH₃CN | | 40° C. | 48 | 12 | <1 h | K[13] CN, D₂O |
| K+ | dibenzylamine | 1:4 | 1:4 | CH₃CN | | 40° C. | 16h | 5 | <1h | |
| K+ | Benzotriazole | 1:4 | 1:4 | CH₃CN | | 48° C. +80° C. | 16 + 1 | 5 | <1h | |

Example 7

Reaction of $P_4O_{10}$ with $K^{13}CN$ and Triethylamine, Followed by Hydrolysis and Catalytic Hydrogenation Using 5% Rh/C and HCl to Produce AMPA In dry acetonitrile (7 mL), phosphoric anhydride (0.35 g, 1.233 mmol) was stirred with triethylamine (0.70 g, 6.9 mmol) for 10 minutes. At the end of this time, $K^{13}CN$ (0.35 g, 5.3 mmol) was added and stirring was continued for 16 hours at 25° C. The volatile components were removed under reduced pressure, and pH 2 buffer (2 ML) was added. This mixture was shaken until homogeneous, then allowed to stand for 3 days at room temperature. After this time, the solution was stored at 4° C. for 3 days. The $^{31}P$ NMR spectrum showed the presence of cyanophosphonate (30.2%) and cyanopolyphosphates (16.8%). This mixture was placed in an autoclave, after which water (100 ml) was added, followed by 5% Rh/C (Strem, 140 mg), then HCl-dioxane (4N, 2.5 mL, 10 mmol). The autoclave was then sealed, purged once with nitrogen, and pressurized with hydrogen to 1000 psi. The reaction was stirred overnight (19 hours). At the end of this time, the hydrogen pressure was released, the autoclave was pressurized once with nitrogen, the pressure was released and the autoclave was opened. The collected reaction mixture was filtered, stirred with Chelex resin, filtered again and analyzed by HPLC (phosphate detection method). The yield of AMPA was 32.6% by HPLC, based on phosphorus equivalents charged as phosphoric anhydride. The $^{31}P$ NMR was consistent with this formulation. It is expected that the AMPA yield in this product solution will increase with further treatment, for example, with the addition of a suitable amount of acid or base and appropriate heating.

Example 8

General Procedure for Low Pressure Hydrogenations

Dipotassium cyanophosphonate (0.133 g, 1.0 mmol) was added to Raney nickel (0.118 g, as a 50% slurry in water, W2 form) in a Fisher Porter bottle containing a stir bar. Water (5 mL) was added, and platinum tetrachloride (0.105 g, 0.31 mmol) was added. The pressure bottle was immediately connected to a hydrogen manifold, and three purges with hydrogen at 75 psi were done, and the bottle was pressurized to 75 psi. The reaction mixture was vigorously stirred for 25.5 hours at room temperature. The pressure was then released and the reaction mixture was filtered. HPLC analysis determined a 63% yield of aminomethylphosphonic acid.

Example 9

General Procedure for Hydrogenation in Autoclave

In a 300 mL Autoclave Engineers autoclave, $Na_2O_3PCN$ $(H_2O)_{0.49}$ (0.80 g, 5.0 mmol) was added, followed by 10% Pt/C (0.15 g), water (100 mL) and then HCl.dioxane (2.5 mL, 4N, 10.0 mL). The autoclave was sealed, pressured once with nitrogen above 500 psi, vented and pressured with hydrogen to 1001 psi. Stirring at about 1500 rpm was started. Within about 10 minutes, the internal pressure was about 996 psi, and the autoclave internal temperature was about 26° C. After stirring overnight, the hydrogen was vented, the autoclave was repressurized with nitrogen and vented, and then the reactor was opened and the reaction mixture removed. The reaction mixture was filtered, and the resulting solution analyzed by HPLC. The yield by HPLC of aminomethylphosphonic acid was 85%, and the yield by $^{31}P$ NMR was 87%.

Example 10

Preparation of Phosphonitrile Derivatives from Phosphoric Anhydride and Hydrocyanic Acid As a general example, under an inert atmosphere, 1 molar part of $P_4O_{10}$ was mixed with a dry polar solvent ($CH_3CN$ is preferred, 4 mL per mmol $P_4O_{10}$) and a few molar parts (four parts are preferable) of a dry aprotic base were added. The mixture was then heated at 30°–40° C. to effect partial or total dissolution of $P_4O_{10}$ (about 5 to 10 minutes), after which several molar parts (four parts are preferable) of dry liquid $H^{12}CN$ or $H^{13}CN$ or a mixture of both were added to this solution cooled in an ice bath with magnetic stirring. The mixture was heated at the specified temperature, usually between 30° and 80° C., for the specified time period, often between 2 and 20 hours. At the end of this time period, the solution was purged by nitrogen for 2 hours to remove free HCN. The rest of the volatile compounds were removed using a vacuum pump then the viscous residue was hydrolyzed by water or buffer. The yield of cyanophosphonate derivatives was analyzed before and after hydrolysis.

In a particular example, the reaction was carried out in 8 ml of $CH_3CN$ with $P_4O_{10}$ (0.56 g, 1.97 mmol), quinuclidine (0.89 g, 8.0 mmol) and $H^{13}CN$ (0.4 mL, 10 mmol) at 48° C. for 16 hours, giving a homogeneous solution. After purging with nitrogen, $^{31}P$ NMR showed the presence of 87.6% of P—CN containing species (major signals correspond to cyclic tricyanotripolyphosphonate: $^{31}P$ NMR ($CH_3CN$) −35 ppm (dt, $^1J_{PC}$=187.7 Hz, $^3J_{PC}$=11.0 Hz), $^{13}C$ NMR ($CH_3CN$) 120.3 ppm (doublet of triplets, $^1J_{CP}$=187.2 Hz, $^3J_{CP}$=11.0 Hz) and dicyanotripolyphosphate $^{31}P$ NMR ($CH_3CN$) −34.5 ppm (dd, $^1J_{PC}$=184.6 Hz, $^3J_{PP}$=19.8 Hz), $^{13}C$ NMR ($CH_3CN$) 121.3 ppm (dd, $^1J_{CP}$=184.4 Hz, $^3J_{CP}$= 2.0 Hz). Part of the $CH_3CN$ solution was hydrolyzed in water (4:1, $CH_3CN$:$H_2O$) yielding the same ratio of products. The solvent of another portion of unhydrolyzed reaction mixture was removed under reduced pressure. A portion of this solid, 0.1 g, was hydrolyzed in 1 mL of buffer at pH=2 (final pH of medium, 5.0), giving 87.2% of P—CN containing species (cyclic tricyanotripolyphosphonate: $^{31}P$ NMR ($H_2O$) −34 ppm (dt, $^1J_{PC}$=202.9 Hz, $^3J_{PC}$=11.0 Hz), $^{13}C$ NMR ($H_2O$) 117.2 ppm (dt, $^1J_{CP}$=201.8 Hz, $^3J_{CP}$=11.0 Hz) and dicyanotripolyphosphate $^{31}P$ NMR ($H_2O$) −33.2 ppm (dd, $^1J_{PC}$=198.4 Hz, $^3J_{PP}$=21.4Hz), $^{13}C$ NMR($H_2O$) 117.6 ppm ($^1J_{CP}$=198.4 Hz).

Additional representative conditions and yields are shown in Tables VIII–XI.

TABLE VIII

Reactions of HCN and $P_4O_{10}$

| mmol of HCN | mmol of $P_4O_{10}$ | Additive (mmol) | Temp °C. | Time before hydrolysis | Solvent | Yield P-CN (%) before hydrolysis | Yield P-CN (%) after hydrolysis (final pH or solvent) |
|---|---|---|---|---|---|---|---|
| 12.95 | 3.0 | $NEt_3$(12) | 40 | 16h | $CH_3CN$ | 62 | 60 (pH = 3.0) 51 (pH = 9.0) |
| 12.95[1] | 3.0 | $NEt_3$(12) | 40 | 7d | $CH_3CN$ | 66 | 62 (pH = 3.0) |
| 12.95 | 3.17 | 4-t-BuPy (12.6) | 40 | 18h | $CH_3CN$ | 63 | 36 (pH = 3.0) 47 (pH = 6.0) |
| 15.5 | 1.50 | 4-t-BuPy (6.0) | 70 + 40 | 1 + 16h | $CH_3CN$ | 40 | 22 (pH = 7.0) |
| 5.18 | 0.50 | none | 40 | 16h | $CH_3CN$ | 0 | 0 |
| 12.95 | 3.0 | $NEt_3$(2.0) | 50 | 48h | $C_6H_5CN$ | 0 | 0 |
| 46.6 | 0.5 | none | 34 | 20h | none | 0 | 0 |
| 15.6 | 3.0 | TMED (12.0) | 80 | 16h | $CH_3CN$ | 72 | 68.2 (in $CH_3CN$) 28.6 (pH = 1.0) |
| 15.6 | 3.0 | TMED (12.0) + $NEt_3$(12.0) | 70 + 40 | 1 + 16h | $CH_3CN$ | 64.6 | 62.1 (in $CH_3CN$) |
| 15.6 | 3.0 | Proton-Sponge (11.7) | 80 | 16h | $CH_3CN$ | 67 | 48.7 (in $CH_3CN$) |
| 14.26 | 2.47 | TEBD (8.84) | 45 | 16h | $CH_3CN$ | 55.7 | 51.0 (in $CH_3CN$) |
| 10.37 | 3.24 | DBU (10.0) | 80 | 16h | $CH_3CN$ | 41.8 | 41.2 (in $CH_3CN$) |
| 9.07 | 1.80 | Quinuclidine (7.1) | 48 | 16h | $CH_3CN$ | 84.9 | 84.7 (in $CH_3CN$) 79.1 #H = 6.0) |
| 11.7 | 2.22 | $NBu_3$(9.12) | 40 | 64h | $CH_3CN$ | 68.3 | 61.6 (in $CH_3CN$) |
| 17.5 | 2.22 | Quinuclidine (8.02) | 48 | 16h | $CH_3CN$ | 82.2 | 75.4 (in $CH_3CN$) |
| 10.0 | 1.97 | Quinuclidine (8.0) | 48 | 16h | $CH_3CN$ | 87.6 | 87.6 (in $CH_3CN$) 87.2 (pH = 5) |

[1]Same reaction as above at different reaction times
$NEt_3$ is triethyl amine.
4-t-BuPy is 4-tert-butylpyridine.
TMED is N,N,N',N'-tetramethylethylenediamine.
Proton sponge ® is 1,8-bis(dimethylamino)naphthalene.
TEED is N,N,N',N'-tetraethylethylenediamine.
DBU is 1,8-diazabicyclo[5.4.0]undec-7-ene.
$NBu_3$ is tri-n-butylamine.

TABLE IX

Reactions of HCN and $P_4O_{10}$ in acetonitrile

| Run | $P_4O_{10}$ Eq. | HCN Eq. | Base Eq. | Base | Temp °C | Time h | P-CN % Yield Before hydrolysis | P-CN % Yield After hydrolysis |
|---|---|---|---|---|---|---|---|---|
| 1 | 1 | 5 | 4 | N-Methyl Pyrrolidine | 48 | 19 | 85.3 | 85 (MeCN) |
| 2 | 1 | 5.07 | 4.0 | TMED | 48 | 19 | 80 | 78 (MeCN) 74 (+10 min) 70(+1 h) |
| 3 | 1 | 7 | 4 | TMED | 48 | 19 | 65 | 43 (MeCN) |
| 4 | 1 | 6.1 | 3.7 | t-Butyl-N=P[N(CH$_2$)$_4$]$_3$ | 48 | 19 | 43 | 27 (MeCN) |
| 5 | 1 | 5.24 | 4.0 | MeN(C$_6$H$_{11}$)$_2$ | 30 | 19 | 41 | 34 (MeCN) |

TABLE X

Reactions of HCN and $P_4O_{10}$ in acetonitrile with quinuclidine

| Run | $P_4O_{10}$ Eq. | HCN Eq. | Base Eq. | Base | Temp °C | Time h | P-CN % Yield Before hydrolysis | P-CN % Yield After hydrolysis |
|---|---|---|---|---|---|---|---|---|
| 1[1] | 1 | 4.7 | 3.9 | Quinuclidine | 46 | 19 | 88.2 | 87 (MeCN) |
| 2 | 1 | 4.9 | 4.1 | Quinuclidine | 45 | 19 | 87.2 | 86 (MeCN) |
| 3 | 1 | 5.6 | 4.0 | Quinuclidine | 48 | 19 | 87.1 | nd |

TABLE X-continued

Reactions of HCN and $P_4O_{10}$ in acetonitrile with quinuclidine

| Run | $P_4O_{10}$ Eq. | HCN Eq. | Base Eq. | Base | Temp °C. | Time h | P-CN % Yield Before hydrolysis | P-CN % Yield After hydrolysis |
|---|---|---|---|---|---|---|---|---|
| 4 | 1 | 4.0 | 4.0 | Quinuclidine | 48 | 19 | 83.8 | 79 (in 10 min) 43 (6 h, pH 1.5) |
| 5 | 1 | 5.0 | 4.0 | Quinuclidine | 48 | 19 | 82 | nd |

[1]Hydrogenation step used 1 eq HC
[2]$P_4O_{10}$ and HCN and quinuclidine at 0° C. initially

TABLE XI

Hydrogenation of HCN, $P_4O_{10}$ and quinuclidine reaction mixtures at 1000 psi with 5% Rh/C catalyst according to conditions of hydrolysis.

| Reaction & Hydrolysis | Temp. | Time, h | Hydrolysis Condition | % Yield AMPA HPLC | NMR | % Yield Phosphate HPLC | NMR |
|---|---|---|---|---|---|---|---|
| 1A[1] | RT | 20 + 1 wk as HPLC sample | pH = 1.7 | 27.7 | | 4.7 | |
| 1B | 138° | 2 | pH = 1.7 | 79.3 (avg. of 3) | 82 | 21.5 | 18 |
| 2A[2] | RT | | pH = 5.6 | 21.7 | 33 | 0 | 0 |
| 2B | 134 | 2 | pH = 5.6 | 59.4 | 58 | 16.0 | 16 |
| 2C | 134 | 5 | pH = 5.6 | 70.5 (avg. of 2) | 68 | 18.0 | 17 |
| 2D | 134 | 8 | pH = 5.6 | 74.1 | 70 | 18.3 | 17 |
| 2E | 100 | 16 | pH = 5.6 | 71.7 | 73 | 17 | 18 |
| 2F | 130 | 2 | pH = 11.8 | 75.5 | 71 | 8.5 | 9 |
| 2G | 130 | 39 | pH = 11.8 | 80.0 | 78 | 14.1 | 13 |
| 2H | 130 | 3 | pH = 1.5 | 80.7 (avg. of 2) | 80 | 19.4 | 20 |

[1]Runs beginning with number "1" are from HCN/$P_4O_{10}$ reaction of Run 2 in Table X
[2]Runs beginning with number "2" are from HCN/$P_4O_{10}$ reaction of Run 1 in Table X

Example 11

Conversion of Phosphoric Anhydride to AMPA

Phosphoric anhydride was treated with potassium cyanide and amine following the procedure No. 6 using about 1.25 mmol of phosphoric anhydride. At the end of this reaction, the solvent was removed under reduced pressure. For the 1 h hydrolyses, the resulting powder was added to water (100 mL) in an autoclave containing hydrogen chloride-dioxane (10 mmol) and 5% Rh/C (122 to 139 milligrams), and was hydrogenated at about 1000 psi overnight at room temperature following the procedure No. 8. For the 2 and 3 day hydrolyses, hydrolysis took place at room temperature, then, the hydrolysis mixture was kept at the indicated temperature for the rest of the hydrolysis time. The hydrogenation was then performed as for the short hydrolysis time experiments. After the pressure was released and the system purged with nitrogen, the reaction mixture was filtered, and the amount of AMPA was determined by HPLC. The reaction mixtures were then heated to the temperature specified below for the period of time indicated, and the amount of AMPA was determined. In the following Table IX, the hydrolysis time refers to the duration of the hydrolysis prior to the start of the hydrogenation; n.d. indicates that a yield was not determined.

TABLE XII

Reaction Conditions and Yield for Conversion of $P_4O_{10}$ to AMPA

| $P_4O_{10}$ Expt. | Amine | Hydrolysis Time | Yield $O_3PCN$ | Yield Cyanopoly-phosphates | AMPA Yield, no heating | AMPA Yield, with heating | Temp °C. | Time |
|---|---|---|---|---|---|---|---|---|
| 1 | $NEt_3$ | 3 days, rt | 30% | 17% | 33% | 38% | 85 | 4h |
| | | | | | | 46% | 85 | 1 day |
| 2 | t-BuPyr | 1 h, rt | 10% | 61% | 32% | 56% | 85 | 1 day |
| | | 2 days, rt, then 4° C. | 38% | 29% | 44% | 57% | 85 | 1 day |

TABLE XII-continued

Reaction Conditions and Yield for Conversion of $P_4O_{10}$ to AMPA

| $P_4O_{10}$ Expt. | Amine | Hydrolysis Time | Yield $O_3$PCN | Yield Cyanopoly-phosphates | AMPA Yield, no heating | AMPA Yield, with heating | Temp °C. | Time |
|---|---|---|---|---|---|---|---|---|
| 3 | t-BuPyr | 1 h, rt | n.d. | n.d. | 21% | 66% | 118 | 2 h |
| | | | | | | 73% | 118 | 4.5 h |

While the compositions and methods of this invention have been described in terms of preferred embodiments, it will be apparent to those of skill in the art that variations can be applied to the process described herein without departing from the concept, spirit and scope of the invention. All such similar substitutes and modifications apparent to those skilled in the art are deemed to be within the spirit, scope and concept of the invention.

What is claimed is:

1. A process for preparing a cyanophosphonate derivative comprising contacting phosphoric anhydride and a cyanide in a reaction mixture under sufficient conditions to produce a cyanophosphonate derivative.

2. The process of claim 1, wherein the cyanide is soluble in the reaction mixture.

3. The process of claim 1, wherein the cyanide is hydrogen cyanide, an alkali metal cyanide, an alkaline earth metal cyanide, an ammonium cyanide, a tetraalkyl ammonium cyanide, a tetraalkyl phosphonium cyanide, tetraaryl phosphonium cyanide, a trialkyl sulfonium cyanide, a cyanide of a cationic form of an organic amine or mixtures thereof.

4. The process of claim 3, wherein the cyanide is hydrogen cyanide, potassium cyanide, sodium cyanide, lithium cyanide, silver cyanide, gold cyanide, copper cyanide, tetrabutylammonium cyanide or mixtures thereof.

5. The process of claim 4, wherein the cyanide is hydrogen cyanide, potassium cyanide, sodium cyanide, tetrabutylammonium cyanide or mixtures thereof.

6. The process of claim 1, wherein the molar ratio of the cyanide to phosphoric anhydride added to the reaction mixture is from about 1 to about 15.

7. The process of claim 6, wherein the molar ratio of the cyanide to phosphoric anhydride added to the reaction mixture is in the range of about 2 to about 10.

8. The process of claim 7, wherein the molar ratio of the cyanide to phosphoric anhydride added to the reaction mixture is in the range of about 3.5 to about 8.5.

9. The process of claim 1, wherein the temperature of the reaction mixture is in the range of about −20° C. to about 150° C.

10. The process of claim 9, wherein the temperature of the reaction mixture is in the range of about 0° C. to about 90° C.

11. The process of claim 1, wherein the reaction time ranges from about 0.1 to about 50 hours.

12. The process of claim 11, wherein the reaction time ranges from about 0.5 to about 20 hours.

13. The process of claim 12, wherein the reaction time ranges from about 1 to about 6 hours.

14. The process of claim 1, wherein the reaction mixture further contains a solvent.

15. The process of claim 14, wherein the solvent is a polar solvent.

16. The process of claim 14, wherein the solvent is acetonitrile, phenylacetonitrile, adiponitrile, propionitrile, dimethylacetonitrile or mixtures thereof.

17. The process of claim 16, wherein the solvent is acetonitrile, phenylacetonitrile or adiponitrile.

18. The process of claim 1, wherein the reaction mixture further comprises a Lewis base.

19. The process of claim 1, wherein the Lewis base is triethylamine, diglyme, 4-dimethylaminopyridine, tris[2-(2-methoxyethoxy)ethyl]amine, 4-tert-butylpyridine, 4-(5-nonyl)pyridine, trimethylamine, 1,8-bis(dimethylamino) naphthalene, 4-ethylpyridine, phenanthroline, N,N,N',N'-tetramethylethylenediamine, 1,4,7,10,13-pentamethyl-1,4,7, 10,13-pentaazacyclopentadecane, quinuclidine, N-methylpyrrolidine, 1,4-diazobicyclo[2.2.2]octane, 1-butylimidazole, 3-benzylpyridine, 1,5-pentamethylenetetrazole, tris[2(2-methoxyethoxy)ethyl] amine, N,N-dimethylaniline, collidine, N-benzylidine aniline, triphenyl-phosphine or mixtures thereof.

20. The process of claim 19, wherein the Lewis base is 4-tert-butylpyridine, 4-(5-nonyl)pyridine, quinuclidine or N-methylpyrrolidine.

21. The process of claim 18, wherein the molar ratio of Lewis base to phosphoric anhydride added to the reaction mixture is in the range of about 1 to about 10.

22. The process of claim 21, wherein the molar ratio of Lewis base to phosphoric anhydride added to the reaction mixture is in the range of about 2 to about 8.

23. The process of claim 22, wherein the molar ratio of Lewis base to phosphoric anhydride added to the reaction mixture is in the range of about 3 to about 6.

24. The process of claim 1, wherein the process further comprises quenching the reaction solution with water, a buffer or an alcohol to produce a cyanophosphonate derivative.

25. The process of claim 24, wherein the cyanophosphonate derivative is cyanophosphonic acid, a cyanophosphonate monoester monoacid, a cyanophosphonate monosalt monoester, a cyanophosphonate diester, a cyanophosphonate monosalt monoacid or a cyanophosphonate disalt.

26. The process of claim 1, wherein the cyanophosphonate derivative is a cyclic cyanophosphonate anhydride, a linear cyanophosphonate anhydride, a mixed linear cyanophosphonatephosphate anhydride or a mixed cyclic cyanophosphonatephosphate anhydride.

27. The process of claim 1, wherein the cyanophosphonate derivative is potassium hydrogen cyanophosphonate, potassium methyl cyanophosphonate, potassium ethyl cyanophosphonate, potassium benzyl cyanophosphonate, sodium hydrogen cyanophosphonate, sodium methyl cyanophosphonate, sodium ethyl cyanophosphonate, sodium benzyl cyanophosphonate, lithium hydrogen cyanophosphonate, lithium methyl cyanophosphonate, lithium ethyl cyanophosphonate, lithium benzyl cyanophosphonate, methyl hydrogen cyanophosphonate, ethyl hydrogen cyanophosphonate, disodium cyanophosphonate, dipotassium cyanophosphonate, dilithiumcyanophosphonate, bis(2-hydroxyethylammonium)cyanophosphonate, bis (ammonium)cyanophosphonate, bis(isopropylammonium) cyanophosphonate, bis(dimethylammonium) cyanophosphonate, mono(isopropylammonium) cyanophosphonate or bis(trimethylsulfonium) cyanophosphonate.

28. The method of claim 26, wherein the cyanophosphonate derivative is monocyanopyrophosphate, dicyanopyrophosphate, dicyanotripolyphosphate, dicyanotetrapolyphosphate, monocyanotetrapolyphosphate, monocyanopentapolyphosphate, cyanophosphate cyclotrimer or cyanophosphate cyclotetramer.

29. The method of claim 26, wherein the cyanophosphonate derivative is provided in a product mixture from a reaction of phosphoric anhydride and a cyanide.

30. The method of claim 26, wherein the cyanophosphonate derivative is provided in a product mixture from a reaction of a pyrophosphate ester and a cyanide.

31. The method of claim 26, wherein the cyanophosphonate derivative is provided in a product mixture from a reaction of a phosphate ester and a cyanide.

32. A process for preparing an aminomethylphosphonate derivative comprising the steps of
  contacting phosphoric anhydride and a cyanide in a reaction mixture under sufficient conditions to produce a cyanophosphonate derivative; and
  hydrogenating the cyanophosphonate derivative in the presence of a suitable catalyst under sufficient conditions to produce an aminomethylphosphonate derivative.

33. The process of claim 32, wherein the cyanophosphonate derivative is cyanophosphonic acid, a cyanophosphonate monoester monoacid, a cyanophosphonate monosalt monoester, a cyanophosphonate diester, a cyanophosphonate monosalt monoacid or a cyanophosphonate disalt.

34. The process of claim 32, wherein the cyanophosphonate derivative is a cyclic cyanophosphonate anhydride, a linear cyanophosphonate anhydride, a mixed linear cyanophosphonate-phosphate anhydride or a mixed cyclic cyanophosphonate-phosphate anhydride.

35. The process of claim 32, wherein the cyanophosphonate derivative is potassium hydrogen cyanophosphonate, potassium methyl cyanophosphonate, potassium ethyl cyanophosphonate, sodium hydrogen cyanophosphonate, sodium methyl cyanophosphonate, sodium ethyl cyanophosphonate, lithium hydrogen cyanophosphonate, lithium methyl cyanophosphonate, lithium ethyl cyanophosphonate, methyl hydrogen cyanophosphonate, ethyl hydrogen cyanophosphonate, disodium cyanophosphonate, dipotassium cyanophosphonate, dilithiumcyanophosphonate, bis(2-hydroxyethylammonium)cyanophosphonate, bis(ammonium)cyanophosphonate, bis(isopropylammonium) cyanophosphonate, bis(dimethylammonium) cyanophosphonate, mono(isopropylammonium) cyanophosphonate or bis(trimethylsulfonium) cyanophosphonate.

36. The process of claim 32, wherein the cyanophosphonate derivative is monocyanopyrophosphate, dicyanopyrophosphate, dicyanotripolyphosphate, dicyanotetrapolyphosphate, monocyanotetrapolyphosphate, monocyanopentapolyphosphate, cyanophosphate cyclotrimer or cyanophosphate cyclotetramer.

37. The process of claim 32, wherein the catalyst is a cobalt-containing compound, a nickel-containing compound, a rhodium-containing compound, a platinum-containing compound, or a palladium-containing compound.

38. The process of claim 32, wherein the catalyst is Raney cobalt, Raney nickel, platinum tetrachloride ($PtCl_4$) promoted Raney nickel, platinum on carbon, palladium on carbon or rhodium on carbon.

39. The process of claim 38, wherein the catalyst is a Raney nickel catalyst.

40. The process of claim 38, wherein the catalyst is a platinum promoted Raney nickel catalyst.

41. The process of claim 40, wherein the catalyst is a platinum tetrachloride ($PtCl_4$) promoted Raney nickel catalyst.

42. The process of claim 38, wherein the catalyst is rhodium on carbon, platinum on carbon or palladium on carbon.

43. The method of claim 42, wherein the hydrogenation reaction mixture further contains an acid.

44. The method of claim 43, wherein the acid is an inorganic acid.

45. The method of claim 44, wherein the inorganic acid is hydrochloric acid, sulfuric acid, phosphoric acid, nitric acid or hydrocyanic acid.

46. The method of claim 45, wherein the inorganic acid is hydrochloric acid.

47. The method of claim 43, wherein the acid is an organic acid.

48. The method of claim 47, wherein the organic acid is acetic acid, trifluoroacetic acid, trifluoromethanesulfonic acid or p-toluenesulfonic acid.

* * * * *